(12) United States Patent
Blok

(10) Patent No.: US 10,334,844 B2
(45) Date of Patent: Jul. 2, 2019

(54) ANTI FUNGAL AND ANTI-MICROBIAL PROTECTION FOR STORAGE ITEMS AND PROTECTIVE COVERS

(75) Inventor: Johannes Blok, Perth Amboy, NJ (US)

(73) Assignee: BROADWAY HOLDINGS IV, LLC, Monroe, NJ (US)

( * ) Notice: Subject to any disclaimer, the term of this patent is extended or adjusted under 35 U.S.C. 154(b) by 323 days.

(21) Appl. No.: 12/657,012

(22) Filed: Jan. 12, 2010

(65) Prior Publication Data
US 2010/0175796 A1  Jul. 15, 2010

Related U.S. Application Data

(60) Provisional application No. 61/204,936, filed on Jan. 12, 2009.

(51) Int. Cl.
*A01N 25/34* (2006.01)
*B65D 81/24* (2006.01)

(52) U.S. Cl.
CPC .............. *A01N 25/34* (2013.01); *B65D 81/24* (2013.01)

(58) Field of Classification Search
None
See application file for complete search history.

(56) References Cited

U.S. PATENT DOCUMENTS

| 4,761,328 A * | 8/1988 | Shin ............................. 428/220 |
| 5,503,840 A * | 4/1996 | Jacobson ............... A01N 25/26 424/404 |
| 6,015,816 A * | 1/2000 | Kostyniak et al. ........... 514/299 |
| 7,081,285 B1 * | 7/2006 | Barre et al. ................... 428/35.2 |
| 2002/0000289 A1 * | 1/2002 | Nickell et al. ........... 156/244.13 |
| 2005/0053784 A1 * | 3/2005 | Wood et al. ................... 428/372 |
| 2005/0131100 A1 * | 6/2005 | Herbst ................... A01N 31/08 523/122 |
| 2006/0012200 A1 * | 1/2006 | Kohn ................... B65D 33/065 294/152 |
| 2007/0006391 A1 * | 1/2007 | Ghosh .................... D01F 1/103 8/115.51 |

FOREIGN PATENT DOCUMENTS

WO   WO-2008-089822   *   7/2009

OTHER PUBLICATIONS

Shimura H, An antifungal compound involved in symbiotic germination of *Cypripedium macranthos* var *rebumense* (Orchidaceae), 68, 2007, 1442-1447.*

* cited by examiner

*Primary Examiner* — Celeste A Roney
(74) *Attorney, Agent, or Firm* — Philip M. Weiss; Weiss & Weiss

(57) ABSTRACT

Anti fungal and anti-microbial protection for storage items and protective covers.

7 Claims, No Drawings

ANTI FUNGAL AND ANTI-MICROBIAL PROTECTION FOR STORAGE ITEMS AND PROTECTIVE COVERS

RELATED APPLICATIONS

The present invention is based on provisional application Ser. No. 61/204,936 filed Jan. 12, 2009.

FIELD OF THE INVENTION

The present invention relates to anti fungal and anti-microbial protection for storage items and protective covers.

SUMMARY OF THE INVENTION

The present invention relates to anti fungal and anti-microbial protection for storage items and protective covers. It is an object of the present invention for the storage items to comprise storage bags. It is an object of the present invention for the protective covers to comprise covers for mattresses, furniture and rugs. It is an object of the present invention for the storage items and covers to comprise poly-olefins, such as polyethylene and polypropylene. It is an object of the present invention for the anti-microbial/anti-fungal properties to be derived from natural compounds that are extracted from plants. It is an object of the present invention for the plants to be lusianthrin and chrysin. It is an object of the present invention for the compounds to be chemical in nature.

It is an object of the present invention for the anti-fungal and anti-microbial agents to be copper (II) 8-quinolinolate (CAS No. 10380-28-6); zinc oxide (CAS No. 1314-13-2); zinc-dimethyl dithiocarbamate (CAS No. 137-304); 2-mercaptobenzothiazole, zinc salt (CAS No. 155-04-4); barium metaborate (CAS No. 13701-59-2); tributyl tin benzoate (CAS No. 4342-36-3); bis tributyl tin salicylate (CAS No. 22330-14-9); tributyl tin oxide (CAS No. 56-35-9); parabens: ethyl parahydroxybenzoate (CAS No. 120-47-8); propyl parahydroxybenzoate (CAS No. 94-13-3); methyl parahydroxybenzoate (CAS No. 99-76-3); and butyl parahydroxybenzoate (CAS No. 94-26-8); methylenebis(thiocyanate) (CAS No. 6317-18-6); 1,2-benzisothiazoline-3-one (CAS No. 2634-33-5); 2-mercaptobenzo-thiazole (CAS No. 149-30-4); 5-chloro-2-methyl-3 (2H)-isothiazolone (CAS No. 57373-19-0); 2-methyl-3(2H)-isothiazolone (CAS No. 57373-20-3); zinc 2-pyridinethiol-N-oxide (CAS No. 1346341-7); tetra-hydro-3,5-di-methyl-2H-1,3,5-thiadiazine-2-thione (CAS No. 533-74-4); N-trichloromethyl-thio-4-cyclohexene-1,2-dicarboximide (CAS No. 133-06-2); 2-n-octyl-4-isothiazoline-3-one (CAS No. 26530-20-1); 2,4,5,6-tetrachloro-isophthalonitrile (CAS No. 1897-45-6); 3-iodo-2-propynyl butylcarbamate (CAS No. 55406-53-6); diiodomethyl-p-tolylsulfone (CAS No. 20018-09-1); N-(trichloromethyl-thio)phthalimide (CAS No. 133-07-3); potassium N-hydroxy-methyl-N-methyl-dithiocarbamate (CAS No. 51026-28-9); sodium 2-pyridinethiol-1-oxide (CAS No. 15922-78-8); 2-(thiocyanomethylthio) benzothiazole (CAS No. 21564-17-0); 2-4(-thiazolyl)benzimidazole (CAS No. 148-79-8).

It is an object of the present for the anti-microbial agents and/or anti-fungal agents to be mixed with the resins in a suitable concentration and extruded on a blown or cast film extruder.

It is an object of the present invention for the bags and covers to protect contents from molds and fungi that ordinarily form over time in a closed storage environment.

DETAILED DESCRIPTION OF THE INVENTION

An anti fungal and anti-microbial compound which is included in storage items and protective covers. The storage items comprise storage bags. The protective covers to comprise covers for mattresses, furniture and rugs. The storage items and covers comprise poly-olefins, such as polyethylene and polypropylene. In an embodiment, the anti-microbial/anti-fungal properties are derived from natural compounds that are extracted from plants. In an embodiment, the plants are lusianthrin and chrysin. In an embodiment, the compounds are chemical in nature.

The anti-fungal and anti-microbial agents are comprised of copper (II) 8-quinolinolate (CAS No. 10380-28-6); zinc oxide (CAS No. 1314-13-2); zinc-dimethyl dithiocarbamate (CAS No. 137-304); 2-mercaptobenzothiazole, zinc salt (CAS No. 155-04-4); barium metaborate (CAS No. 13701-59-2); tributyl tin benzoate (CAS No. 4342-36-3); bis tributyl tin salicylate (CAS No. 22330-14-9); tributyl tin oxide (CAS No. 56-35-9); parabens: ethyl parahydroxybenzoate (CAS No. 120-47-8); propyl parahydroxybenzoate (CAS No. 94-13-3); methyl parahydroxybenzoate (CAS No. 99-76-3); and butyl parahydroxybenzoate (CAS No. 94-26-8); methylenebis(thiocyanate) (CAS No. 6317-18-6); 1,2-benzisothiazoline-3-one (CAS No. 2634-33-5); 2-mercapto-benzo-thiazole (CAS No. 149-30-4); 5-chloro-2-methyl-3 (2H)-isothiazolone (CAS No. 57373-19-0); 2-methyl-3 (2H)-isothiazolone (CAS No. 57373-20-3); zinc 2-pyridinethiol-N-oxide (CAS No. 1346341-7); tetra-hydro-3,5-di-methyl-2H-1,3,5-thiadiazine-2-thione (CAS No. 533-74-4); N-trichloromethyl-thio-4-cyclohexene-1,2-dicarboximide (CAS No. 133-06-2); 2-n-octyl-4-isothiazoline-3-one (CAS No. 26530-20-1); 2,4,5,6-tetrachloro-isophthalonitrile (CAS No. 1897-45-6); 3-iodo-2-propynyl butylcarbamate (CAS No. 55406-53-6); diiodomethyl-p-tolylsulfone (CAS No. 20018-09-1); N-(trichloromethyl-thio)phthalimide (CAS No. 133-07-3); potassium N-hydroxy-methyl-N-methyl-dithiocarbamate (CAS No. 51026-28-9); sodium 2-pyridinethiol-1-oxide (CAS No. 15922-78-8); 2-(thiocyanomethylthio) benzothiazole (CAS No. 21564-17-0); 2-4(-thiazolyl)benzimidazole (CAS No. 148-79-8) alone or in combination.

In an embodiment, anti-microbial agents and/or anti-fungal agents are mixed with the resins in a suitable concentration and extruded on a blown or cast film extruder.

The treated bags and covers protect contents from molds and fungi that ordinarily form over time in a closed storage environment.

The invention claimed is:
1. An anti-fungal and/or anti-microbial protection for storage items comprising:
   a device for storing articles for storage;
   said device consisting of polyethylene mixed with an agent;
   said agent selected from the group consisting of: barium metaborate; zinc 2-pyridinethiol-N-oxide; sodium 2-pyridinethiol-1-oxide; 5-chloro-2-methyl-3(2H)-isothiazolone; 2-methyl-3(2H)isothiazolone; N-trichloromethyl-thio-4-cyclohexene-1,2-dicarboximide; bis tributyl tin salicylate; methylenebis(thiocyanate); 3-iodo-2-propynyl butylcarbamate; alone or in combination;
   said agent used in a suitable concentration to act as anti-fungal and/or anti-microbial protection for said articles for storage;

said storage articles consisting of mattresses, furniture and rugs.

2. The item of claim 1 wherein said storage items comprise storage bags.

3. The item of claim 1 wherein said agent has anti-microbial/anti-fungal properties derived from natural compounds that are extracted from plants.

4. The item of claim 3 wherein said plants are lusianthrin and chrysin.

5. The item of claim 1 wherein said agents are chemical in nature.

6. The item of claim 2 wherein said bags protect said storage articles from molds and fungi that form over time in a closed storage environment.

7. An anti-fungal and/or anti-microbial protection for storage items comprising:
  a device for storing articles for storage;
  said device consisting of polyethylene mixed with an agent, said agent mixed with resins;
  said agent selected from the group consisting of: barium metaborate; zinc 2-pyridinethiol-N-oxide; sodium 2-pyridinethiol-1-oxide; 5-chloro-2-methyl-3(2H)-isothiazolone; 2-methyl-3(2H)-isothiazolone; N-trichloromethyl-thio-4-cyclohexene-1,2-dicarboximide; bis tributyl tin salicylate; methylenebis(thiocyanate); 3-iodo-2-propynyl butylcarbamate; alone or in combination;
  said agent used in a suitable concentration to act as anti-fungal and/or anti-microbial protection for said articles for storage;
  said storage articles consisting of mattresses, furniture and rugs.

* * * * *